(12) United States Patent
Luthra et al.

(10) Patent No.: US 6,406,687 B1
(45) Date of Patent: *Jun. 18, 2002

(54) NON-THROMBOGENIC AND ANTI-THROMBOGENIC POLYMERS

(76) Inventors: Ajay Kumar Luthra, 219 Somervell Road, South Harrow, Middlesex HA2 8UA; Shivpal Singh Sandhu, 63 Lascelles Road, Slough, Berkshire SL3 7PW, both of (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,701

(22) Filed: Nov. 4, 1998

(51) Int. Cl.$^7$ .................. A61K 31/765; A61K 31/74; A61K 31/785; A61K 31/795

(52) U.S. Cl. .................. 424/78.37; 424/78.18; 424/78.31; 424/78.35

(58) Field of Search .................. 424/78.01, 78.37, 424/78.18, 78.31, 78.35

(56) References Cited

U.S. PATENT DOCUMENTS

| | | |
|---|---|---|
| 3,086,956 A | 4/1963 | Armen et al. |
| 4,200,563 A | 4/1980 | Komiya |
| 4,521,564 A | 6/1985 | Solomon et al. |
| 4,755,379 A | 7/1988 | Jozefonvicz et al. |
| 4,840,851 A | 6/1989 | Gölander et al. |
| 5,216,087 A | 6/1993 | Kim et al. |
| 5,510,418 A | 4/1996 | Rhee et al. |
| 5,529,986 A | 6/1996 | Larsson et al. |
| 5,697,972 A | 12/1997 | Kim et al. |
| 6,096,798 A * | 8/2000 | Luthra et al. ............... 523/105 |

FOREIGN PATENT DOCUMENTS

| | | |
|---|---|---|
| EP | 0 656 215 A1 | 6/1995 |
| WO | WO 91/16932 | 11/1991 |
| WO | WO 97/41164 | 11/1997 |

* cited by examiner

Primary Examiner—Thurman K. Page
Assistant Examiner—Humera N. Sheikh
(74) Attorney, Agent, or Firm—Thompson Coburn LLP

(57) ABSTRACT

The invention provides a medical device which comprises a polymer coating. The polymer coating comprises a polymer comprising a polymer backbone and having at least two pendant groups selected from: (a) a polyoxyalkylene ether group, (b) a sulphate group, (c) a sulphonate group, or (d) a sulphamate group, and the polymer is produced by polymerizing monomers having such groups.

10 Claims, No Drawings

NON-THROMBOGENIC AND ANTI-THROMBOGENIC POLYMERS

SUMMARY OF THE INVENTION

This invention relates to the synthesis of polymers which contain non-thrombogenic (NON-TB) as well as anti-thrombogenic (ANTI-TB) properties. Such polymers can be conveniently represented as follows:

| POLYMER BACKBONE | | POLYMER BACKBONE | |
|---|---|---|---|
| ) | and | ) | ) |
| ( | | ( | ( |
| [NON-TB] | | [NON-TB] | [ANTI-TB] |
| Type 1 | | Type 2 | |

In schematic diagrams of this kind, as used herein, the designated side chains or groups can occur in any order and in any relative proportions along the polymer backbone.

In polymers of Type 1 the non-thrombogenic (NON-TH) component may consist of non-ionic hydrophilic domains, ionic domains, zwitterionic domains or combinations of such domains. In novel Type 1 polymers in accordance with the invention, such non-thrombogenic components may be selected from, but are not limited to, polymerizable sulphonates, polymerizable sulphates, polymerizable N-sulphates (also known as sulphamates), polymerizable zwitterionic compounds, and polymerizable polyethylene glycols. When we synthesized polymers of Type 1, without the anti-thrombogenic component, and coated various medical devices, we found blood cell and protein deposition reduced by greater than 90%. Greatly reduced (>95%) activation of white cells, platelets and complement was observed. This type of synthetic polymer can be described as a non-thrombogenic polymer.

The non-thrombogenic Type 1 polymer, as described, was synthesized with polymerizable heparin to give a Type 2 polymer. Surprisingly, the activity of the heparin was retained in the Type 2 polymer and such polymers, when coated on to medical devices, had the additional property of reducing the thrombin-antithrombin complex concentration. This inclusion of heparin into the non-thrombogenic polymer gave a new polymer which additionally exhibited anti-thrombogenic properties.

Another aspect of this invention is the process by which the non-thrombogenic and anti-thrombogenic polymers are coated onto medical devices.

BACKGROUND OF THE INVENTION

There is a growing interest in the use of artificial materials in clinical practice where these materials are in continuous contact with blood. Medical devices made from these materials are required to perform in the harsh biological environment in a specific application, for a specific duration without stimulating a biological response which may prove to be detrimental. Hence, such devices are required to be accepted by the biological environment for a specific application and duration, i.e., need to be bioacceptable. Improvements in bioacceptability are highly desirable for medical devices manufactured from artificial materials. Such materials commonly include polyvinyl chloride, polyethylene, polypropylene, polyurethanes, polycarbonates, stainless steel, silicones and the like. The biological response to blood contact with an artificial surface can be regarded in terms of different contributions from protein, platelet and blood cell deposition, together with platelet and blood activation leading to thrombus formation.

Many investigations have been carried out to prevent an artificial surface from provoking thrombus formation, i.e., to form a bioacceptable surface. Such investigations include the use of polymers which are natural, hydrophilic, hydrophobic, zwitterionic and charged (anionic and cationic). These types of polymers are non-thrombogenic, have had limited success and therefore application. Surface modification of an artificial material by heparin (i.e., formation of an anti-thrombogenic surface) has also proved to be intractable. Although clot formation has been reduced, platelet activation and blood cell activation are however still prevalent. Similarly, a particular artificial surface may be resistant to protein, platelet and blood cell deposition but may still activate blood constituents.

Each surface, whether non-thrombogenic or anti-thrombogenic, has its own profile of desirable bioacceptable properties, but no particular material possesses the full spectrum of the desired properties.

Additional disadvantages of some of the known approaches are (i) the procedures used to produce these materials are complex, (ii) the methods of applying these materials to the medical device are elaborate, and (iii) these processes utilize reagents which are highly toxic, even in minute quantities.

In a new approach to the problem of finding suitable bioacceptable materials, we have synthesized a novel non-thrombogenic polymer, and have also modified non-thrombogenic polymers by incorporating a polymerizable anti-thrombogenic compound, exemplified by polymerizable heparin. It was found that heparin activity was maintained, while the non-thrombogenity of the polymer component was prevalent. Other known biologically active anti-thrombogenic compounds include hirudin, warfarin and hyaluronic acid, and can be used in the same manner as the polymerizable heparin.

SUMMARY OF THE INVENTION

The invention provides a medical device which comprises a polymer coating, the polymer coating comprising a polymer comprising a polymer backbone and having at least two pendant groups selected from:
- (a) a polyoxyalkylene ether group,
- (b) a sulphate group,
- (c) a sulphonate group, or
- (d) a sulphamate group, wherein the polymer is produced by polymerizing monomers having such groups.

The invention also provides a medical device which comprises a polymer coating, the polymer coating comprising a polymer comprising a polymer backbone and having at least two pendant groups selected from:
- (a) a polyoxyalkylene ether group,
- (b) a sulphate group,
- (c) a sulphonate group,
- (d) a sulphamate group, or
- (e) a zwitterionic group, wherein the polymer coating is produced by polymerizing monomers having such groups.

The invention provides a polymer comprising a polymer backbone and having at least two pendant groups selected from:
- (a) a polyoxyalkylene ether group,
- (b) a sulphate group, (c) a sulphonate group, or (d) a sulphamate group, wherein the polymer further comprises a pendant heparin group, and wherein the polymer is produced by polymerizing monomers having such groups.

Additional features and advantages of the invention are set forth in the description which follows and in part will be apparent from the description. The objectives and other advantages of the invention will be realized and attained by the medical devices, polymers, coatings, and methods of the invention as particularly pointed out in the written description and claims.

It is to be understood that both the foregoing general description and the following detailed description are exemplary and explanatory and are intended to provide further explanation of the invention as claimed.

DETAILED DESCRIPTION OF PREFERRED EMBODIMENTS

The invention provides a medical device which comprises a polymer coating, the polymer coating comprising a polymer comprising a polymer backbone and having at least two pendant groups selected from:

(a) a polyoxyalkylene ether group, (b) a sulphate group, (c) a sulphonate group, or (d) a sulphamate group, wherein the polymer is produced by polymerizing monomers having such groups. In one embodiment of the invention, the polymer comprises a pendant polyoxyalkylene ether group. In another embodiment of the invention, the polymer does not comprise a pendant sulphonate group. In yet another embodiment of the invention, the polymer comprises a pendant polyoxyalkylene ether group and does not comprise a pendant sulphonate group. In one embodiment of the invention, the medical device is a blood oxygenator. In one embodiment of the invention, the polymer comprises a pendant heparin group; in another, the polymer comprises a pendant hirudin, warfarin, or hyaluronic acid group.

The invention provides a method of making a medical device which comprises a polymer coating comprising:

providing a mixture of monomers comprising at least two of the following monomers:

(a) a monomer having a polyoxyalkylene ether group, (b) a monomer having a sulphate group, (c) a monomer having a sulphonate group, or (d) a monomer having a sulphamate group;

coating the mixture of monomers onto a medical device; and polymerizing the mixture of monomers to form a polymer coating, wherein the mixture of monomers can comprise only monomers or can be partially prepolymerized. In one embodiment of the invention, the polymer comprises a pendant polyoxyalkylene ether group. In another embodiment of the invention, the polymer does not comprise a pendant sulphonate group. In yet another embodiment of the invention, the polymer comprises a pendant polyoxyalkylene ether group and does not comprise a pendant sulphonate group. In one embodiment of the invention, the medical device is a blood oxygenator. In one embodiment of the invention, the polymer comprises a pendant heparin group; in another, the polymer comprises a pendant hirudin, warfarin, or hyaluronic acid group.

The invention provides a medical device which comprises a polymer coating, the polymer coating comprising a polymer comprising a polymer backbone and having at least two pendant groups selected from:

(a) a polyoxyalkylene ether group, (b) a sulphate group, (c) a sulphonate group, (d) a sulphamate group, or (e) a zwitterionic group, wherein the polymer coating is produced by polymerizing monomers having such groups. In one embodiment of the invention, the polymer comprises a pendant polyoxyalkylene. ether group. In another embodiment of the invention, the polymer does not comprise a pendant sulphonate group. In yet another embodiment of the invention, the polymer comprises a pendant polyoxyalkylene ether group and does not comprise a pendant sulphonate group. In one embodiment of the invention, the medical device is a blood oxygenator. In one embodiment of the invention, the polymer comprises a pendant heparin group; in another, the polymer comprises a pendant hirudin, warfarin, or hyaluronic acid group.

The invention provides a polymer comprising a polymer backbone and having at least two pendant groups selected from:

(a) a polyoxyalkylene ether group, (b) a sulphate group, (c) a sulphonate group, or (d) a sulphamate group, wherein the polymer further comprises a pendant heparin group, and wherein the polymer is produced by polymerizing monomers having such groups. In one embodiment of the invention, the polymer comprises a pendant polyoxyalkylene ether group. In another embodiment of the invention, the polymer does not comprise a pendant sulphonate group. In yet another embodiment of the invention, the polymer comprises a pendant polyoxyalkylene ether group and does not comprise a pendant sulphonate group. The invention also provides a coating material comprising the polymer described above.

The invention also provides a polymer comprising a polymer backbone and having at least two pendant groups selected from:

(a) a polyoxyalkylene ether group, (b) a sulphate group, (c) a sulphonate group, or (d) a sulphamate group, wherein the polymer further comprises a pendant hirudin, warfarin, or hyaluronic acid group, and wherein the polymer is produced by polymerizing monomers having such groups.

One embodiment of the present invention provides polymers comprising a polymer backbone having pendant groups, obtainable by polymerizing monomers having such groups, characterized in that said polymers are obtained by copolymerizing monomers of at least three different classes selected from:

(a) monomers having sulphate groups (b) monomers having sulphonate groups (c) monomers having sulphamate groups, and (d) monomers having polyoxyalkylene ether groups.

Another embodiment of the present invention provides polymers comprising a polymer backbone having pendant groups, obtainable by polymerizing monomers having such groups, characterized in that said polymers are obtained by copolymerizing monomers of at least three different classes selected from:
  (a) monomers having sulphate groups
  (b) monomers having sulphonate groups
  (c) monomers having sulphamate groups
  (d) monomers having polyoxyalkylene ether groups, and
  (e) monomers having zwitterionic groups.

A further embodiment of the present invention provides a method of forming a coating of a polymer as described above on a medical device by forming an ungelled partial polymer by reacting a solution of an amine polymer with a crosslinking agent, activating the medical device by solution coating with said partial polymer, and depositing the polymer on the resulting activated medical device.

The present invention also provides a coating material comprising a polymer as described above.

Without wishing to be bound by any theory or explanation of the invention, it appears that non-thrombogenic surfaces have an important impact on the first event of contact of blood with an artificial surface. This event occurs almost instantaneously and consists of protein adsorption. Subsequent events are largely determined by interactions of blood with the adsorbed protein. The nature of the artificial surface determines the manner and extent of protein attachment.

For hydrophobic surfaces, attachment occurs by hydrophobic interactions with the protein, which causes conformational change of the adsorbed protein, exposing sites for protein interaction resulting in further protein adsorption. The next sequence of events has a pronounced influence in promoting platelet adsorption/activation and white cell adsorption/activation. The consequence of these events is the formation of thrombus.

Protein adsorption on hydrophilic surfaces is more readily and rapidly reversible than on hydrophobic surfaces. The extent of reversibility is determined by the nature of the chemical bond in the equilibrium state. At high states of reversibility, protein adsorption is not prevalent and consequently platelet and white cell adsorption/activation is prevented. Therefore, thrombus formation is averted.

This type of hydrophilic surface is regarded as being non-thrombogenic and in this respect we have found a new artificial hydrophilic polymer with at least three different types of hydrophilic groups which include, but are not restricted to, sulphonate, sulphate, N-sulphate (sulphamate) or zwitterionic groups, and polyethylene glycol or glycol ether units in the same polymer backbone.

In one embodiment of the present invention the non-thrombogenic polymer is obtainable by radical polymerization, preferably of monomers having reactive carbon-carbon double bonds to form the polymer backbone and said monomer constituents containing, but not limited to, sulphonates, sulphates, N-sulphates (sulphamates), zwitterions, and polyethylene glycol units, these monomer constituents being contained in the same polymer composition. Such monomers may be separated into three groups.

The first group is based on monomers derived from acrylates or methacrylates of sulphonates, sulphates and N-sulphates:

$$CH_2=CR_1-C(=O)-Z_1-R_2-Y_1-X_1 \qquad 1)$$

Where $R_1$ is H or $CH_3$;
  $R_2$ is a linear or branched alkylene of 2–10 carbon atoms, phenylene, phenyl alkylene with 1–10 carbon atoms in the alkylene structure or the polyoxyalkylene structure $[CH_2CHR_1-O]_n$ where $R_1$ is H or $CH_3$ and n is from 2 to 50; $Z_1$ is oxygen (—O—) to give an ester linkage or secondary amine (—NH—) to give an amide linkage; $Y_1$ is (—O—) or (—NH—) or is absent; and
  $X_1$ is sulphonate (—$SO_3$) together with an acceptable balancing cation.

The second group is based on monomers derived from vinyl, allyl or methyl allyl, of sulphonates, sulphates and N-sulphates:

$$CH_2=CR_1-R_2-Y_1-X_1 \qquad 2)$$

Where $R_1$ is H or $CH_3$; $R_2$ is a linear or branched alkylene of 1–10 carbon atoms, phenylene, phenyl alkylene with 1–10 carbon atoms in the alkylene structure or the polyoxyalkylene structure $[CH_2-CHR_1-O)]_n$, where $R_1$ is H or $CH_3$ and n is from 2 to 50; $Y_1$ is (—O—) (—NH—) or is absent; and $X_1$ is sulphonate (—$SO_3$—) together with an acceptable balancing cation.

In both groups of monomers (1) and (2), when $Y_1$ is (—O—), the monomer terminates in a sulphate group; $Y_1$ is (—NH—), the monomer terminates in a N-sulphate group; $R_2$ and $Y_1$ are not present, the monomer terminates in a sulphonate group; $R_2$ is polyoxyalkylene and $Y_1$ is not present, the monomer terminates in a sulphate group.

The third group of monomers is derived from acrylates or methacrylates of polyoxyalkylene glycols or glycol ethers:

$$CH_2=CR_3-C(=O)-O-[CH_2-CHR_4-O]_n-R_7 \qquad 3)$$

Where $R_3$ and $R_4$, which may be the same or different, are each H or $CH_3$, $R_7$ is H or alkyl with 1 to 5 carbon atoms, e.g., methyl, and n is an integer from 2 to 50.

Monomer examples incorporating sulphonate groups include, but are not restricted to, salts of: 2-sulphoethyl methacrylate, 2-sulphoethyl acrylate, 3-sulphopropyl methacrylate, 3-sulphopropyl acrylate, vinyl sulphonate, allyl sulphonate, methyl allyl sulphonate, p-styrene sulphonate, 2-acrylamido-methylpropanesulphonate, 3-sulphopropyl ethoxy methacrylate, 3-sulphopropyl ethoxy acrylate, 3-sulphopropyl polyoxyalkylene methacrylate, 3-sulphopropyl polyoxyalkylene acrylate.

Similarly, examples of monomers terminating in sulphate groups include, and are not confined to, salts of: 2-sulphatoethyl methacrylate, 2-sulphatoethyl acrylate, 3-sulphatopropyl methacrylate, 3-sulphatopropyl acrylate, 4-sulphatobutyl methacrylate, 4-sulphatobutyl acrylate, allyl sulphate, methyl allyl sulphate, 3-buten-1-sulphate, 3-buten-2-sulphate, 2-methyl-2-propanol-sulphate, 2-methyl-3-buten-1-sulphate, 3-methyl-3-buten-1-sulphate, 2-sulphatoethyl methacrylamide, 2-sulphatoethyl acrylamide, 3-sulphatopropyl methacrylamide, 3-sulphatopropyl acrylamide, 4-sulphatobutyl methacrylamide, 4-sulphatobutyl acrylamide, sulphato polyoxyalkylene methacrylate, sulphato polyoxyalkylene acrylate.

Examples of N-sulphate (sulphamate) containing monomers include, but are not limited to, salts of: 2-sulphamatoethyl methacrylate, 2-sulphamatoethyl acrylate, 3-sulphamatopropyl methacrylate, 3-sulphamatopropyl acrylate, 4-sulphamatobutyl methacrylate, 4-sulphamatobutyl acrylate, allyl sulphamate, methyl allyl sulphamate, 2-sulphamatoethyl methacrylamide, 2-sulphamatoethyl acrylamide, 3-sulphamatopropyl methacrylamide, 3-sulphamatopropyl acrylamide, 4-sulphamatobutyl methacrylamide, 4-sulphamatobutyl acrylamide, sulphamato polyoxyalkylene methacrylate, sulphamato polyoxyalkylene acrylate.

The salts used to form the polymers according to the invention, including those listed above, will have an acceptable, especially physiologically acceptable, balancing cation such as an alkali metal (e.g., sodium) cation, or an ammonium or substituted ammonium cation. Hydrogen cations usually provide a polymer that is too acidic for the preferred use.

Other examples of non-thrombogenic polymers include those in which zwitterionic monomers may be included in the above formulations. For example, the non-thrombogenic polymers can contain any zwitterionic monomer as an integral part of the polymer backbone. The zwitterionic monomers may also be included in the non-thrombogenic/antithrombogenic polymers. Such zwitterionic monomers include, but are not limited to, 2-(methacryloyloxyethyl)-2'-(trimethylammonium) ethyl phosphate inner salt and dimethyl (2-methacryloylethyl)-[1-(2-sulphopropyl)] ammonium betaine inner salt.

A wide range of monomer compositions can be utilized in the formation of the non-thrombogenic polymer. Such a polymer may contain, and is not limited to, 3 to 4 different monomer constituents. The ter-polymer (3 different monomers) and the tetra-polymer (4 different monomers) are formulated from 3 or 4 respectively of at least one sulphate monomer type, at least one sulphonate monomer type, at least one sulphamate monomer type, and at least one polyoxyalkylene monomer type in the final polymer composition. This polymer composition can accordingly be schematically represented as follows, where the relative frequency and the order of occurrence of each monomer type are variable (being random co-polymers). In each instance anions shown are balanced by acceptable cations, such as those mentioned above.

| POLYMER BACKBONE |
| --- |
| a) ter-polymer |
| i) |
| )  )  ) |
| (  (  ( |
| $SO_3-$  $SO_4-$  $[CH_2-CHR_1-O]_n-CH_3$ |
| ii) |
| )  )  ) |
| (  (  ( |
| $NHSO_3-$  $SO_4-$  $[CH_2-CHR_1-O]_n-CH_3$ |
| iii) |
| )  )  ) |
| (  (  ( |
| $NHSO_3-$  $SO_3-$  $[CH_2-CHR_1-O]_n-CH_3$ |
| iv) |
| )  )  ) |
| (  (  ( |
| $NHSO_3-$  $SO_4-$  $SO_3-$ |
| b) tetra-polymer |
| )  )  )  ) |
| (  (  (  ( |
| $NHSO_3-$  $SO_3-$  $SO_4-$  $[CH_2-CHR_1-O]_n-CH_3$ |

The above co-polymerized monomer compositions are examples of non-thrombogenic (NON-TH) polymers represented above as Type 1.

In another aspect of this invention the non-thrombogenic component is accompanied by a polymerizable anti-thrombogenic component such as polymerizable heparin in the same polymer backbone, and said anti-thrombogenic component in its bioactive form being carried by an integral part of the aforementioned polymer backbone.

Functionalization of heparin by methacrylation of heparin is known (ACS Symposium Series 77; Carbohydrate Sulphates, 1978). Subsequent known polymerizations with other monomers give rise to anti-thrombogenic polymers only, containing no non-thrombogenic component (of the kind referred to herein).

This aspect of this invention accordingly provides a polymer containing non-thrombogenic and anti-thrombogenic constituents on the same polymer backbone. Preferred non-thrombogenic constituents may comprise sulphate, sulphamate, sulphonate, zwitterionic and polyoxyalkylene glycol and glycol ether, together with anti-thrombogenic constituents consisting of polymerizable heparin bearing carbon-carbon double bonds. Essentially the carbon-carbon double bond carried by the heparin moiety is polymerizable by a free radical process and may be by way of example vinyl, allyl, methyl allyl, acrylate or polymerizable methacrylate. Heparin linked to a component containing a carbon-carbon double bond is hereafter referred to as heparin monomer, corresponding monomers in which the heparin is replaced by hirudin, warfarin or hyaluronic acid moieties may be used in like manner.

The favored heparin monomers are those in which heparin is linked to a polyoxyalkylene methacrylate or polyoxyalkylene acrylate through an ester or carbonate linkage. The ester or carbonate linkage is formed by activating the hydroxyl terminating polyoxyalkylene methacrylate or acrylate with carbonyldiimidazole, forming the activated imidazoyl carbonate, which subsequently is either coupled to carboxylic groups of the heparin molecule to yield an ester linkage or coupled to hydroxyl groups of the heparin molecule to yield a carbonate linkage. This means of attaching the polyoxyalkylene methacrylate or acrylate group to heparin allows polymerization of the heparin with the desired biological properties. Other coupling techniques as described in WO 91/16932 using 1-ethyl-3-(3-dimethylaminopropyl) carbodiimide result in linkages occurring on sulphate groups of the heparin, called a sulphonamide linkage. This coupling procedure results in poor biological properties since these N-sulphate and sulphate groups are important for binding to antithrombin.

Preferred heparin monomers include those of the following formula:

With ester linkage to heparin:

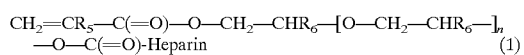

$$CH_2=CR_5-C(=O)-O-CH_2-CHR_6-[O-CH_2-CHR_6-]_n \\ -O-C(=O)\text{-Heparin} \quad (1)$$

With carbonate linkage to heparin:

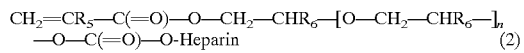

$$CH_2=CR_5-C(=O)-O-CH_2-CHR_6-[O-CH_2-CHR_6-]_n \\ -O-C(=O)-O\text{-Heparin} \quad (2)$$

In both general formulae, $R_5$ and $R_6$, which may be the same or different, are each H or $CH_3$; and n is an integer from 0 to 49.

Particularly preferred heparin monomers are those derived from polyethylene oxide units, that is to say where $R_2$ is H.

The heparin monomers (1) and (2), as above, are novel and are other aspects of this invention and may be produced by reacting hydroxyl terminated polyoxyalkylene with carbonyldiimidazole [Im—C(=O)—Im] to form the activated imidazoyl carbonate: $CH_2=CR_5-C(=O)-O-CH_2-CHR_6-[O-CH_2-CHR_6-]_n-O-C(=O)-Im$, where $R_5$, $R_6$ and n have the meanings given above, this being followed by the coupling of the activated imidazoyl carbonate to heparin under basic pH conditions using bicarbonate buffer at room temperature.

The heparin monomer is polymerized with the aforementioned monomer of sulphate, sulphamate, sulphonate and polyoxyalkylene, producing a polymer with both non-thrombogenic and anti-thrombogenic properties. This polymer composition may contain 4 to 5 of the different types of monomer constituent. The tetra-polymer (4 different monomer types) and the penta-polymer (5 different monomer types) are so formulated from 3 or 4 respectively of at least one sulphate monomer type, at least one sulphonate monomer type, at least one sulphamate monomer type, and at least one polyoxyalkylene monomer type, together with at least one heparin monomer type, in the final polymer composition. This polymer composition can accordingly be schematically represented as follows, the relative frequency and the order of occurrence of each monomer type being variable. In each instance the anions shown are balanced by acceptable cations, such as those mentioned above.

POLYMER BACKBONE a) tetra-polymer i)

)         )         )                              )
(         (         (                              (
$SO_3$—    $SO_4$—    $[CH_2—CHR_1—O]_n—CH_3$         Hep ii)

)         )         )                              )
(         (         (                              (
$NHSO_3$—  $SO_4$—    $[CH_2—CHR_1—O]_n—CH_3$         Hep iii)

)         )         )                              )
(         (         (                              (
$NHSO_3$—  $SO_3$—    $[CH_2—CHR_1—O]_n—CH_3$         Hep iv)

)         )         )                              )
(         (         (                              (
$NHSO_3$—  $SO_4$—    $SO_3$—                         Hep b) penta-polymer )         )         )         )                    )
(         (         (         (                    (
$NHSO_3$—  $SO_3$—   $SO_4$—   $[CH_2—CHR_1—O]_n—CH_3$  Hep These non-thrombogenic/anti-thrombogenic (NON-TH/ANTI-TH) polymers are of the kind represented above as Type 2.

Polymerization may be carried out by conventional aqueous solution polymerization using a water soluble initiator, such as potassium persulphate, after degassing the solution and under an inert gas, such as nitrogen. Reaction temperature for polymerization is at room or elevated temperature, provided that the heparin biological activity is not affected. The preferred polymerization temperature is one between 15 to 90° C., and generally a polymerization temperature of 75° C. is suitable. The polymer may be purified by conventional means, such as precipitation, filtration wash and dialysis.

The aforementioned non-thrombogenic polymer or the non-thrombogenic/anti-thrombogenic polymer according to the invention is capable of being applied as a coating on medical devices for use in blood-contacting applications. In this regard, another aspect of this invention is the modification of polyethylene imine or other primary or secondary amino containing polymers to an extent that they form a stable attachment between the medical device and the non-thrombogenic polymer or the non-thrombogenic—anti-thrombogenic polymer.

The use of unmodified polyethylene imine as an anchoring point for heparin is known, EP 0124676. In these processes the medical device requires chemical pre-treatment to allow attachment of polyethylene imine to occur. Additionally, multi-layers are built up on the device to ensure good coverage and to enhance the stability of the attachment. These are disadvantages which have severe impact on the performance and the coating process. The heparin attached is grafted onto the external polyethylene imine layer where surface covering is limited. There is predominantly preferential ionic bonding of the heparin to the polyethylene imine. In such instances the heparin may be released from the surface. This coating requires repeated steps to ensure that the polyethylene imine is bound effectively. This has the constraint of increasing the complexity of the process which results in high costs being incurred.

To overcome the disadvantages mentioned above we have devised a method for modifying primary or secondary amine polymers including polyethylene imine which can be attached to the medical device without any pre-treatment and can be carried out in a single step. This is achieved by increasing the molecular weight of the amine polymer, but to a limited extent, whereby the polymer does not gel, but remains in solution. This can, for instance, be achieved by crosslinking the amine, e.g., by treatment with a crosslinking agent, such as an alkylene diisocyanate, and/or with an alkyl isocyanate. The isocyanate crosslinking agents mentioned above react very quickly with the amino groups, but other crosslinking agents that are reactive with amino groups may be employed. These include, but are not limited to, diacids, diacid chlorides and cyclic anhydrides or dianhydrides. Generally there will be 4 to 16 carbon atoms between the active groups of the crosslinking agents. By increasing the hydrophobic nature of the amine polymer in this manner, it is capable of attaching to a suitable medical device sufficiently to allow attachment of the non-thrombogenic polymer or the non-thrombogenic/antithrombogenic polymer. Hence the polymer coating process is essentially achieved in two steps, as opposed to multiple steps.

Attachment of the polymer to the polyethylene imine pre-coating can be enhanced by the incorporation of acrolein in the monomer feed for the non-thrombogenic/anti thrombogenic polymer, giving aldehydic groups on the polymer backbone. These products are also novel. The aldehydic groups are allowed to react with amino groups on the modified polyethylene imine to form a Schiff's base which is reduced to form a stable covalent bond. Alternatively the non-thrombogenic/anti-thrombogenic polymer may be attached to the modified polyethylene imine by ionic interaction.

The invention is illustrated by the following Examples, which are not intended to restrict the scope of the invention. In the Examples, concentrations are expressed as percentages weight/volume, i.e. grams per 100 ml of solution.

The structure of the polymers whose preparation is identified in the following Examples can be confirmed by the presence of certain peaks in their FTIR spectra. These peaks include:

| | |
|---|---|
| carbonate | 1745.7 $cm^{-1}$ |
| methacrylate | 870 $cm^{-1}$ and 970 $cm^{-1}$ |
| carboxylic acid (sodium salt or ester) | 1609.8 $cm^{-1}$ |
| carbohydrate hydroxyl | 3500 $cm^{-1}$ |
| C—O—C link in ester | 1250 $cm^{-1}$ |

EXAMPLES 1 TO 5

THE FORMATION OF NON-THROMBOGENIC POLYMERS

EXAMPLE 1

Methoxy polyethyleneglycol methacrylate (MPEG METH., n=13, 9.0 g), ammonium sulphatoethyl methacrylate (25% aqueous solution, 45 g) and vinyl sulphonic acid sodium salt (25% aqueous solution, 13 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

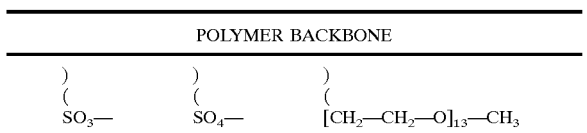

EXAMPLE 2

Methoxy polyethyleneglycol methacrylate (MPEG METH., n=13, 7.7 g), ammonium sulphatoethyl methacrylate (25% aqueous solution, 40.8 g) and 2-sulphamatoethyl methacrylamide (25% aqueous solution, 22.4 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at St. The anionic portion of the polymer composition can be illustrated as follows:

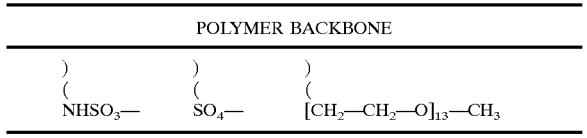

EXAMPLE 3

Methoxy polyethyleneglycol methacrylate (MPEG METH., n=13, 8.6 g), 2-sulphamatoethyl methacrylamide (25% aqueous solution, 45.2 g) and vinyl sulphonic acid sodium salt (25% aqueous solution, 14.4 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

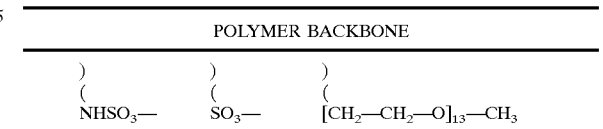

EXAMPLE 4

2-Sulphamatoethyl methacrylamide (25% aqueous solution, 16.0 g), ammonium sulphatoethyl methacrylate (25% aqueous solution, 59.6 g) and vinyl sulphonic acid sodium salt (25% aqueous solution, 18.4 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

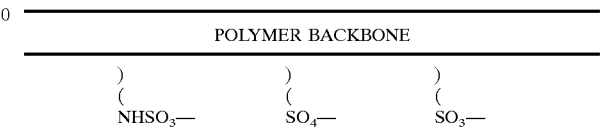

EXAMPLE 5

Methoxy polyethyleneglycol methacrylate (MPEG METH., n=13, 9.3 g), 2-sulphamatoethyl methacrylamide (25% aqueous solution, 17.6 g), ammonium sulphatoethyl methacrylate (25% aqueous solution, 26.4 g) and vinyl sulphonic acid sodium salt (25% aqueous solution, 12.8 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

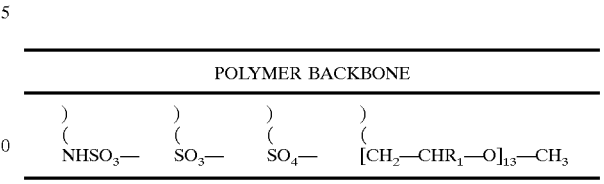

EXAMPLE 6

The Formation of Activated Imidazoyl Carbonate

Hydroxy polyethyleneglycol methacrylate (PEG, n=7, 1.0 g) was added drop-wise to carbonyldiimidazole (Im—C(=

0)—Im; 0.5 g) in anhydrous dichloromethane to form the activated imidazoyl carbonate:

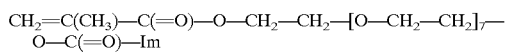

The solution was stirred for 3 hours for the reaction to be completed and dichloromethane was removed on a rotary evaporator.

EXAMPLE 7

Formation of Heparin Monomer

Heparin (injectable grade, 5.0 g) was dissolved in 30 ml of water. The heparin solution was then added to the activated imidazoyl carbonate formed in Example 6. The pH of the solution was adjusted to 8.5 to 9.0 by using potassium bicarbonate and solution was stirred for 24 hours to form the heparin monomer. The solution was then adjusted to pH 7 with HCl.

EXAMPLES 8 TO 12

THE FORMATION OF NON-THROMBOGENIC/ ANTI-THROMBOGENIC POLYMERS

EXAMPLE 8

Methoxy polyethyleneglycol methacrylate (MPEG METH., n=13, 9.0 g), ammonium sulphatoethyl methacrylate (25% aqueous solution, 45 g), vinyl sulphonic acid (25% aqueous solution, 13 g) and the heparin monomer formed Example 7 (5 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

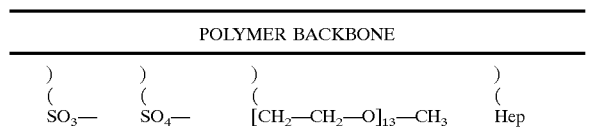

EXAMPLE 9

Methoxy polyethyleneglycol methacrylate (MPEG METH., n=13, 7.7 g), ammonium sulphatoethyl methacrylate (25% aqueous solution, 40.8 g), 2-sulphamatoethyl methacrylamide (25% aqueous solution, 22.4 g) and the heparin monomer formed in Example 7 (5 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10liters of water in cellulose acetate membrane, M.W. cut off at 12,000 to 14,000. The polymer was removed and concentrated to 150 ml and stored at 5° C. The anionic portion of the polymer composition can be illustrated as follows:

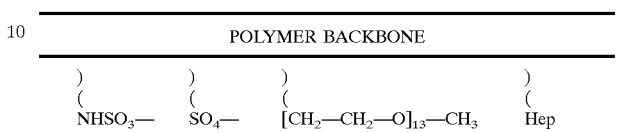

EXAMPLE 10

Methoxy polyethyleneglycol methacrylate (MPEG METH., n=13, 8.6 g), 2-sulphamatoethyl methacrylamide (25% aqueous solution, 45.2 g), vinyl sulphonic acid sodium salt (25% aqueous solution, 14.4 g) and the heparin monomer formed in Example 7 (5 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

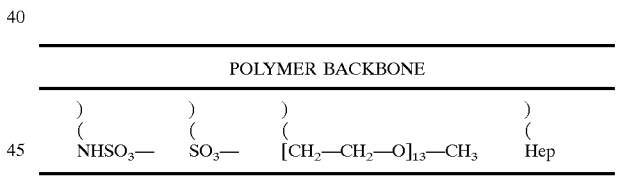

EXAMPLE 11

2-Sulphamatoethyl methacrylamide (25% aqueous solution, 16.0 g), ammonium sulphatoethyl methacrylate (25% aqueous solution, 59.6 g), vinyl sulphonic acid sodium salt (25% aqueous solution, 18.4 g) and the heparin monomer formed in Example 7 (5 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

| POLYMER BACKBONE | | | |
|---|---|---|---|
| )( | )( | )( | )( |
| NHSO$_3$— | SO$_4$— | SO$_3$— | Hep |

EXAMPLE 12

Methoxy polyethyleneglycol methacrylate (MPEG METH., n=13, 9.3 g), 2-sulphamatoethyl methacrylamide (25% aqueous solution, 17.6 g), ammonium sulphatoethyl methacrylate (25% aqueous solution, 26.4 g), vinyl sulphonic acid sodium salt (25% aqueous solution, 12.8 g) and the heparin monomer formed in Example 7 (5 g) were added to a 250 ml conical flask. The contents of the flask were degassed for 30 minutes, followed by bubbling with nitrogen and then heating to 75° C. Potassium persulphate (100 mg) was dissolved in water (15 ml) and added to the flask to start polymerization. The reaction was allowed to continue for 15 minutes after which a very viscous solution was obtained. The reaction was stopped by pouring the contents of the flask into a beaker containing cold water (100 ml). The resultant polymer was dialyzed against 10 liters of water in cellulose acetate membrane, M.W. cut off at 12,000 to 14,000. The polymer was removed and concentrated to 150 ml and stored at 5° C. The anionic portion of the polymer composition can be illustrated as follows:

| POLYMER BACKBONE | | | | | |
|---|---|---|---|---|---|
| )( | )( | )( | )( | | )( |
| NHSO$_3$— | SO$_3$— | SO$_4$— | [CH$_2$—CH$_2$—O]$_{13}$—CH$_3$ | | Hep |

EXAMPLES 13 AND 14

MODIFICATION OF POLYETHYLENE IMINE (PEP)

PEI was supplied as a 50% solution in water by BASF, approximate molecular weight is 20,000.

EXAMPLE 13

PEI (140 g) was dissolved in 1 liter of isopropanol. Hexamethylene diisocyanate (2.8 g) was dissolved in 50 ml of acetone. The diisocyanate solution was added drop-wise to the PEI solution. The final solution was then rotary evaporated to remove the isopropanol (500 ml).

EXAMPLE 14

PEI (140 g) was dissolved in 500 ml of isopropanol. Hexamethylene diisocyanate (1.4 g) was dissolved in 50 ml of acetone. The diisocyanate solution was added drop-wise to the PEI solution. A solution of n-butyl isocyanate (2.0 g in 50 ml acetone) was then added drop-wise to the solution.

EXAMPLES 15 AND 16

FORMATION OF SOLUTION FOR COATING

Five mole percent of acrolein is added to the monomer feed in the formation of the non-thrombogenic polymer or the non-thrombogenic/anti-thrombogenic polymer. This allows chemical linkage to the modified polyethylene imine.

EXAMPLE 15

The modified polyethylene imine as prepared in Example 13 is diluted to give a final composition of 0.23%. The pH of the solution is in the region of 9.5 to 10. Samples of medical devices, generally tubing, connectors and the like are coated by incubating in the solution for 10 minutes, and then washed with distilled water. Typically, the tubing may by polyvinyl chloride, polyethylene or silicone, and the connectors polycarbonate or polyvinyl chloride.

EXAMPLE 16

The non-thrombogenic polymer or the non-thrombogenic/anti-thrombogenic polymer is prepared as in the aforementioned Examples and is diluted with water to give a final polymer concentration of 0.08% (w/v). The pH of the solution is adjusted to 8.5 with sodium tetraborate. After the samples have been incubated in the modified polyethylene imine, as described in Example 15, the samples are incubated in the non-thrombogenic polymer or the non-thrombogenic/anti-thrombogenic polymer for 10 minutes. The samples are then washed and tested for hemocompatibility.

The polymer from Example 1 (non-thrombogenic polymer) and Example 8 (non-thrombogenic/anti-thrombogenic polymer) were assessed for hemocompatibility. The results showed that in both types of polymers, Example 1 (non-thrombogenic polymer) and Example 8 (non-thrombogenic/anti-thrombogenic polymer), when coated on medical devices, the blood cell and protein deposition was reduced by greater than 90% and also greatly reduced (>95%) activation of white cells, platelets and complement activation. Medical devices coated with the product of Example 8 (non-thrombogenic/anti-thrombogenic polymer) showed the additional property of reducing the thrombin-antithrombin complex concentration.

The above description is provided for the purpose of describing embodiments of the invention and is not intended to limit the scope of the invention in any way. It will be apparent to those skilled in the art that various modifications and variations can be made in the medical devices, polymers, coatings, and methods of the invention without departing from the spirit or scope of the invention. Thus, it is intended that the present invention cover the modifications and variations of this invention provided they come within the scope of the appended claims and their equivalents.

What is claimed is:

1. A polymer comprising a polymer backbone and having at least two pendant groups selected from:
    (a) a polyoxyalkylene ether group,
    (b) a sulphate group,
    (c) a sulphonate group, and
    (d) a sulphamate group,
    wherein the polymer further comprises a pendant heparin group, and wherein the polymer is produced by polymerizing monomers having such groups.

2. A polymer of claim 1, wherein the polymer comprises a pendant polyoxyalkylene ether group.

3. A polymer of claim 1, wherein the polymer does not comprise a pendant sulphonate group.

4. A polymer of claim 2, wherein the polymer does not comprise a pendant sulphonate group.

5. A polymer of claim 1, wherein the polymer is produced from at least one of the following monomers having a sulphate group: 2-sulphatoethyl methacrylate, 2-sulphatoethyl acrylate, 3-sulphatopropyl methacrylate, 3-sulphatopropyl acrylate, 4-sulphatobutyl methacrylate, 4-sulphatobutyl acrylate, allyl sulphate, methyl allyl-'sulphate, 3-buten-1-sulphate, 3-buten-2-sulphate, 2-methyl-2-propane- 1-sulphate, 2-methyl-3-buten-1-sulphate, 3-methyl-3-buten-1-sulphate, 2-sulphatoethyl methacrylamide, 2-sulphatoethyl acrylamide, 3-sulphatopropyl methacrylamide, 3- sulphatopropyl acrylamide, 4-sulphatobutyl methacrylamide, 4-sulphatobutyl acrylamide, sulphato polyoxyalkylene methacrylate, and sulphato polyoxyalkylene acrylate.

6. A polymer of claim 1, wherein the polymer is produced from at least one of the following monomers having a pendant sulphonate group: 2-sulphoethyl methacrylate, 2-sulphoethyl acrylate, 3-sulphopropyl methacrylate, 3-sulphopropyl acrylate, vinyl sulphonate, allyl sulphonate, methyl allyl sulphonate, p-styrene sulphonate, 2-acrylamide-methylpropanesulphonate, 3-sulphopropyl ethoxy methacrylate, 3-sulphopropyl ethoxy acrylate, 3-sulphopropyl polyoxyalkylene methacrylate, and 3-sulphopropyl polyoxyalkylene acrylate.

7. A polymer of claim 1, wherein the polymer is produced from at least one of the following monomers having a pendant sulphamate group: 2-sulphamatoethyl methacrylate, 2-sulphamatoethyl acrylate, 3-sulphamatopropyl methacrylate, 3-sulphamatopropyl acrylate, 4-sulphamatobutyl methacrylate, 4-sulphamatobutyl acrylate, allyl sulphamate, methyl allyl sulphamate, 2-sulphamatoethyl methacrylamide, 2-sulphamatoethyl acrylamide, 3-sulphamatopropyl methacrylamide, 3-sulphamatopropyl acrylamide, 4-sulphamatobutyl methacrylamide, 4-sulphamatobutyl acrylamide, sulphamato polyoxyalkylene methacrylate, and sulphamato polyoxyalkylene arcrylate.

8. A polymer of claim 1, wherein the polymer is produced from at least one of the following monomers having a pendant zwitterionic group: 2-(methacryloyloxyethyl)-2'-(trimethylammonium) ethyl phosphate inner salt and (2-methacryloylethyl)- {1-(2-sulphopropyl)} ammonium betaine inner salt.

9. A method of making a polymer which comprises:

providing a mixture of monomers comprising at least two of the following monomers:

(a) a monomer having a polyoxyalkylene ether group, (b) a monomer having a sulphate group, (c) a monomer having a sulphonate group, and (d) a monomer having a sulphamate group;

and further comprising a monomer having a heparin group; and polymerizing the mixture of monomers to form a polymer.

10. A coating material comprising a polymer of claim 1.

\* \* \* \* \*